United States Patent
Tanaka et al.

(10) Patent No.: US 12,066,018 B2
(45) Date of Patent: Aug. 20, 2024

(54) FLUID CONTROL APPARATUS

(71) Applicant: Murata Manufacturing Co., Ltd., Kyoto (JP)

(72) Inventors: Nobuhira Tanaka, Kyoto (JP); Daisuke Kondo, Kyoto (JP); Hiroyuki Yokoi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1044 days.

(21) Appl. No.: 16/991,458

(22) Filed: Aug. 12, 2020

(65) Prior Publication Data

US 2020/0371536 A1    Nov. 26, 2020

Related U.S. Application Data

(63) Continuation of application No. PCT/JP2018/044652, filed on Dec. 5, 2018.

(30) Foreign Application Priority Data

Feb. 16, 2018 (JP) .................. 2018-025664

(51) Int. Cl.
*F04B 45/047* (2006.01)
*A61B 5/0235* (2006.01)
(Continued)

(52) U.S. Cl.
CPC .............. *F04B 45/047* (2013.01); *A61M 1/80* (2021.05); *A61M 1/962* (2021.05); *A61M 39/22* (2013.01);
(Continued)

(58) Field of Classification Search
CPC ....... A61M 39/22; F04B 17/003; F04B 53/10; G05D 16/065
See application file for complete search history.

(56) References Cited

U.S. PATENT DOCUMENTS 4,852,608 A † 8/1989 Bennitt
8,765,311 B2 * 7/2014 Oozu ................ H01M 8/04186
429/502

(Continued)

FOREIGN PATENT DOCUMENTS

JP   2015117647 A   6/2015
JP   2017072140 A   4/2017
(Continued)

OTHER PUBLICATIONS

International Search Report issued in Application No. PCT/JP2018/044652, dated Feb. 19, 2019.
(Continued)

*Primary Examiner* — Craig M Schneider
*Assistant Examiner* — Frederick D Soski
(74) *Attorney, Agent, or Firm* — Pearne & Gordon LLP

(57) ABSTRACT

A fluid control apparatus includes a valve and a pump. The valve has a valve chamber surrounded by the first main plate, the second main plate, and the side plate. The first main plate has a first aperture, and the second main plate has a second aperture. The valve further includes a valve diaphragm disposed inside the valve chamber. The valve diaphragm is configured to switch between a state in which the first aperture and the second aperture communicate with each other and a state in which the first aperture and the second aperture do not communicate with each other. The pump includes a vibration unit that has a piezoelectric device and a vibrating plate. The pump has a pump chamber that is defined by the vibration unit and the second main plate. The pump chamber communicates with the valve chamber through the second aperture.

11 Claims, 4 Drawing Sheets

(51) Int. Cl.
  *A61H 9/00* (2006.01)
  *A61M 1/00* (2006.01)
  *A61M 16/20* (2006.01)
  *A61M 39/22* (2006.01)
  *F04B 17/00* (2006.01)
  *F04B 43/04* (2006.01)
  *F04B 53/10* (2006.01)
  *G05D 16/06* (2006.01)

(52) U.S. Cl.
  CPC .......... *F04B 17/003* (2013.01); *F04B 43/046* (2013.01); *F04B 53/10* (2013.01); *G05D 16/065* (2013.01); *A61B 5/0235* (2013.01); *A61B 2217/005* (2013.01); *A61H 9/00* (2013.01); *A61M 1/743* (2021.05); *A61M 1/964* (2021.05); *A61M 16/20* (2013.01)

(56) References Cited

U.S. PATENT DOCUMENTS

| | | | | |
|---|---|---|---|---|
| 8,835,068 | B2* | 9/2014 | Hasebe | H01M 8/04201 429/513 |
| 9,051,931 | B2* | 6/2015 | Locke | F04B 43/046 |
| 9,234,518 | B2* | 1/2016 | Locke | F04B 51/00 |
| 2009/0010780 | A1* | 1/2009 | Kamitani | F04B 43/046 417/480 |
| 2009/0148318 | A1* | 6/2009 | Kamitani | F04B 45/04 417/413.2 |
| 2009/0232683 | A1* | 9/2009 | Hirata | F04B 45/047 417/413.2 |
| 2009/0242813 | A1* | 10/2009 | Hirata | F16K 31/005 251/129.01 |
| 2011/0070110 | A1* | 3/2011 | Hirata | F04B 43/043 417/413.2 |
| 2011/0076170 | A1* | 3/2011 | Fujisaki | F04B 45/047 417/415 |
| 2011/0127459 | A1* | 6/2011 | Takahashi | F16K 99/0048 251/333 |
| 2012/0244454 | A1* | 9/2012 | Maeda | F16K 15/141 429/513 |
| 2013/0071269 | A1* | 3/2013 | Fujisaki | F04B 43/095 417/413.2 |
| 2013/0178752 | A1* | 7/2013 | Kodama | F16K 15/145 600/498 |
| 2013/0255801 | A1* | 10/2013 | Hirata | F16K 31/1266 137/505.14 |
| 2014/0286795 | A1* | 9/2014 | Kamitani | F04B 49/007 417/62 |
| 2015/0034847 | A1* | 2/2015 | Kotani | F04B 45/047 251/57 |
| 2015/0038858 | A1* | 2/2015 | Ariga | A61B 5/02255 600/490 |
| 2015/0060012 | A1* | 3/2015 | Kamitani | F04B 43/046 165/59 |
| 2015/0167664 | A1* | 6/2015 | Yokoi | F04B 53/109 417/571 |
| 2015/0174910 | A1 | 6/2015 | Kaneko | |
| 2015/0322969 | A1* | 11/2015 | Tanaka | E21B 43/121 417/55 |
| 2016/0076537 | A1* | 3/2016 | Kawamura | F16K 7/12 137/565.11 |
| 2016/0271305 | A1* | 9/2016 | Kurihara | A61M 1/73 |
| 2017/0035951 | A1* | 2/2017 | Tanaka | A61M 1/0693 |
| 2017/0138357 | A1 | 5/2017 | Kondo et al. | |
| 2018/0223829 | A1 | 8/2018 | Tanaka et al. | |
| 2023/0235732 | A1* | 7/2023 | Kawabata | F04B 43/046 417/413.2 |

FOREIGN PATENT DOCUMENTS

| | | |
|---|---|---|
| WO | 2010/139918 A1 | 12/2010 |
| WO | 2010/139918 B1 † | 12/2010 |
| WO | 2017061349 A1 | 4/2017 |

OTHER PUBLICATIONS

Written Opinion issued in Application No. PCT/JP2018/044652, dated Feb. 19, 2019.

\* cited by examiner
† cited by third party

FLUID CONTROL APPARATUS

This is a continuation of International Application No. PCT/JP2018/044652 filed on Dec. 5, 2018 which claims priority from Japanese Patent Application No. 2018-025664 filed on Feb. 16, 2018. The contents of these applications are incorporated herein by reference in their entireties.

BACKGROUND OF THE DISCLOSURE

Field of the Disclosure

The present disclosure relates to a fluid control apparatus for controlling flow rate of fluid.

Description of the Related Art

Various fluid control apparatuses equipped with a driving device, such as a piezoelectric device, have been in practical use.

Patent Document 1 describes a fluid control apparatus having a pump chamber and a valve chamber. According to Patent Document 1, the flow rate of a fluid increases when a gap at the center of the pump chamber and a gap at the center of the valve chamber change in the opposite phase.
Patent Document 1: Japanese Unexamined Patent Application Publication No. 2017-72140

BRIEF SUMMARY OF THE DISCLOSURE

The fluid control apparatus described in Patent Document 1, however, has a structure that enables only one of a top plate and an outer plate that constitute the valve chamber to vibrate. Accordingly, the change in the gap in the valve chamber is small. In other words, the fluid control apparatus does not enjoy an advantage of the gaps changing in the opposite phase, which may not provide a desirable flow rate.

Accordingly, an object of the present disclosure is to provide a fluid control apparatus that enables a fluid to flow efficiently at an improved flow rate.

A fluid control apparatus according to the present disclosure includes a valve and a pump. The valve includes a first main plate, a second main plate having one principal surface that opposes one principal surface of the first main plate, and a side plate that connects the first main plate and the second main plate to each other. The valve has a valve chamber surrounded by the first main plate, the second main plate, and the side plate. The first main plate has a first aperture through which the valve chamber communicates with the outside of the valve chamber, and the second main plate has a second aperture through which the valve chamber communicates with the outside of the valve chamber. The valve further includes a valve diaphragm disposed inside the valve chamber. The valve diaphragm is configured to switch between a state in which the first aperture and the second aperture communicate with each other and a state in which the first aperture and the second aperture do not communicate with each other.

The pump includes a vibration unit that has a piezoelectric device and a vibrating plate and is disposed so as to oppose the other principal surface of the second main plate. The pump has a pump chamber that is defined by the vibration unit and the second main plate. The pump chamber communicates with the valve chamber through the second aperture.

In addition, in flexural vibration of the vibration unit, a frequency coefficient of the first main plate is smaller than a frequency coefficient of the second main plate.

With this configuration, the first main plate having a smaller frequency coefficient is more flexible than the second main plate. In addition, the first main plate and the second main plate vibrate substantially in the opposite phase. This facilitates vibration of the first main plate, which thereby increases a gap height of the valve chamber and facilitates opening and closing of the valve. In other words, this enables the fluid control apparatus to provide a greater flow rate and to improve performance.

A fluid control apparatus according to the present disclosure includes a valve and a pump. The valve includes a first main plate, a second main plate having one principal surface that opposes one principal surface of the first main plate, and a side plate that connects the first main plate and the second main plate to each other. The valve has a valve chamber surrounded by the first main plate, the second main plate, and the side plate. The first main plate has a first aperture through which the valve chamber communicates with the outside of the valve chamber, and the second main plate has a second aperture through which the valve chamber communicates with the outside of the valve chamber. The valve further includes a valve diaphragm disposed inside the valve chamber. The valve diaphragm is configured to switch between a state in which the first aperture and the second aperture communicate with each other and a state in which the first aperture and the second aperture do not communicate with each other.

The pump includes a vibration unit that has a piezoelectric device and a vibrating plate and is disposed so as to oppose the other principal surface of the second main plate. The pump has a pump chamber that is defined by the vibration unit and the second main plate. The pump chamber communicates with the valve chamber through the second aperture.

In addition, the first main plate and the second main plate are made of the same material, and the thickness of the first main plate is smaller than the thickness of the second main plate in a direction normal to respective principal surfaces.

With this configuration, the first main plate becomes more flexible than the second main plate. This facilitates vibration of the first main plate, which thereby increases the gap height of the valve chamber and facilitates opening and closing of the valve. In other words, this enables the fluid control apparatus to provide a greater flow rate and to further improve performance.

In the fluid control apparatus of the present disclosure, a frequency coefficient ratio of the first main plate to the second main plate is preferably greater than 0.85 and smaller than 1.

This facilitates vibration of the first main plate, which thereby increases the gap height of the valve chamber and further facilitates opening and closing of the valve.

The first main plate of fluid control apparatus of the present disclosure preferably has a plurality of the first apertures. In addition, a gap between the first main plate and the second main plate is preferably smaller than a minimum opening width of each first aperture.

With this configuration, the flow path resistance when the valve is open is reduced, which increases the flow rate.

In the fluid control apparatus of the present disclosure, the gap between the first main plate and the second main plate is smaller than a gap between the vibration unit and the second main plate.

This improves the pressure in the valve chamber and further increases the flow rate and improves the flow rectifying effect.

The fluid control apparatus of the present disclosure is applied to a medical apparatus.

The performance of the medical apparatus is thereby improved. The medical apparatus is, for example, a sphygmomanometer, a massage machine, an aspirator, a nebulizer, or a device for negative pressure wound therapy.

Accordingly, the present disclosure can provide a fluid control apparatus that enables a fluid to flow efficiently at an improved flow rate.

DETAILED DESCRIPTION OF THE DISCLOSURE

First Embodiment

Figure 1A:
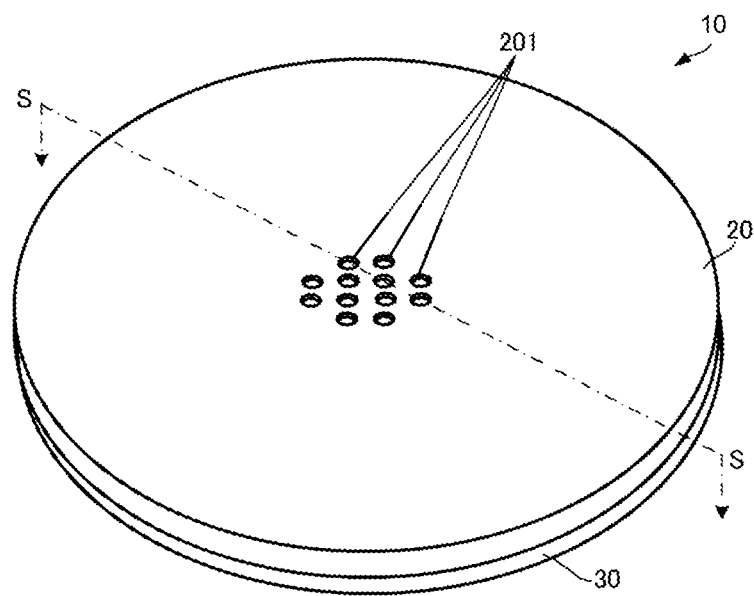
FIG. 1A is a perspective view illustrating the exterior of a fluid control apparatus 10 according to a first embodiment of the present disclosure when the fluid control apparatus 10 is viewed from the side of a valve 20.
Figure 1B:
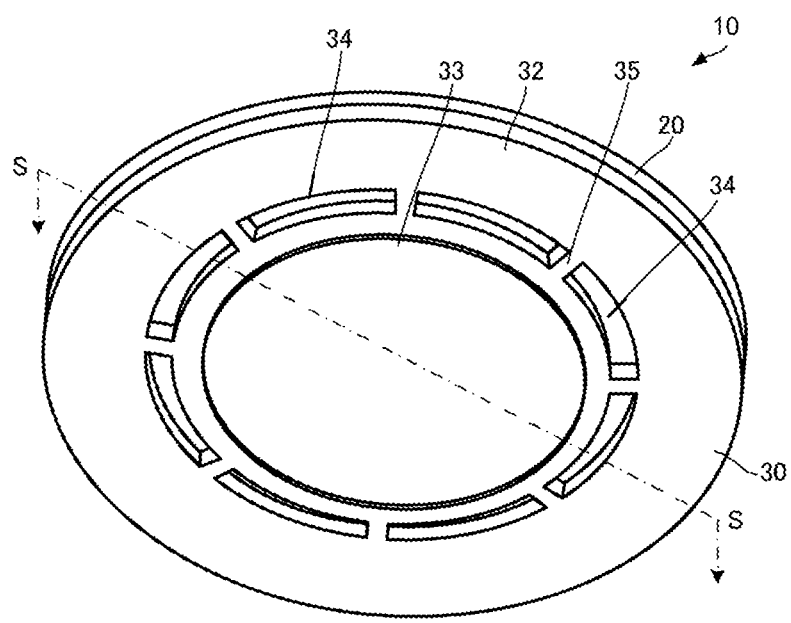
FIG. 1B is a perspective view illustrating the exterior of the fluid control apparatus 10 according to the first embodiment of the present disclosure when the fluid control apparatus 10 is viewed from the side of a pump 30.
Figure 2:
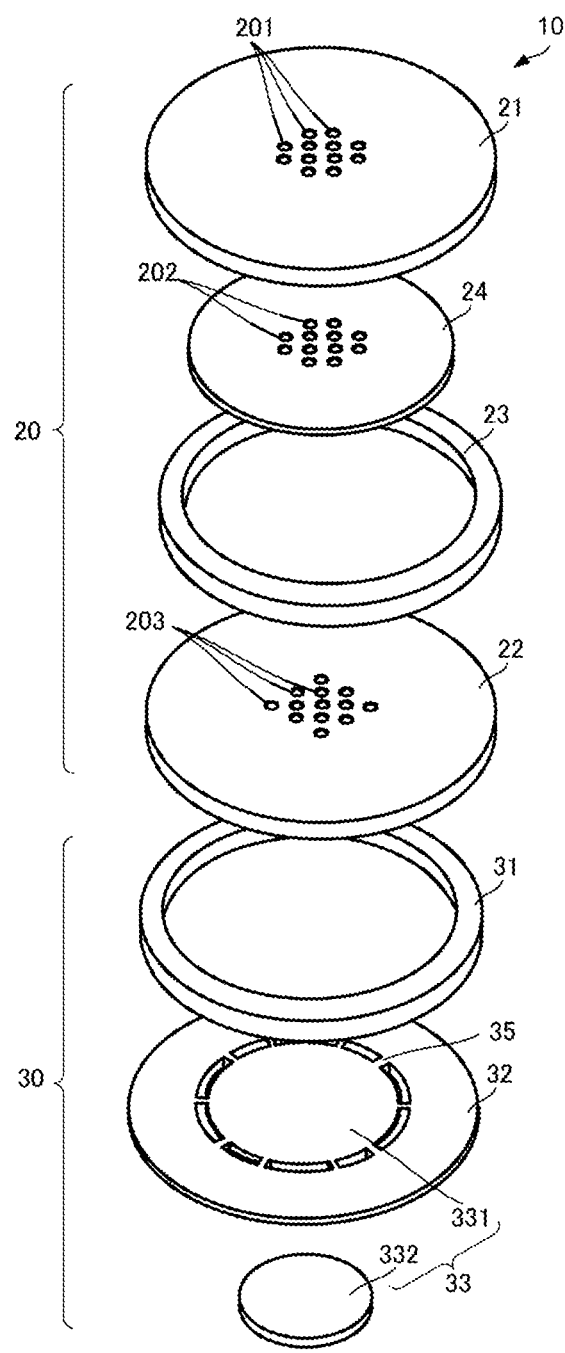
FIG. 2 is an exploded perspective view illustrating the fluid control apparatus 10 according to the first embodiment of the present disclosure.
Figure 3:
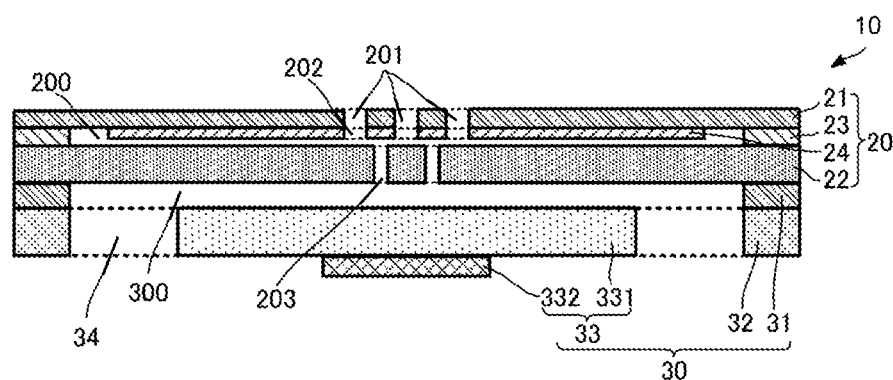
FIG. 3 is a cross-sectional side view illustrating the fluid control apparatus 10 according to the first embodiment of the present disclosure.
Figure 4:
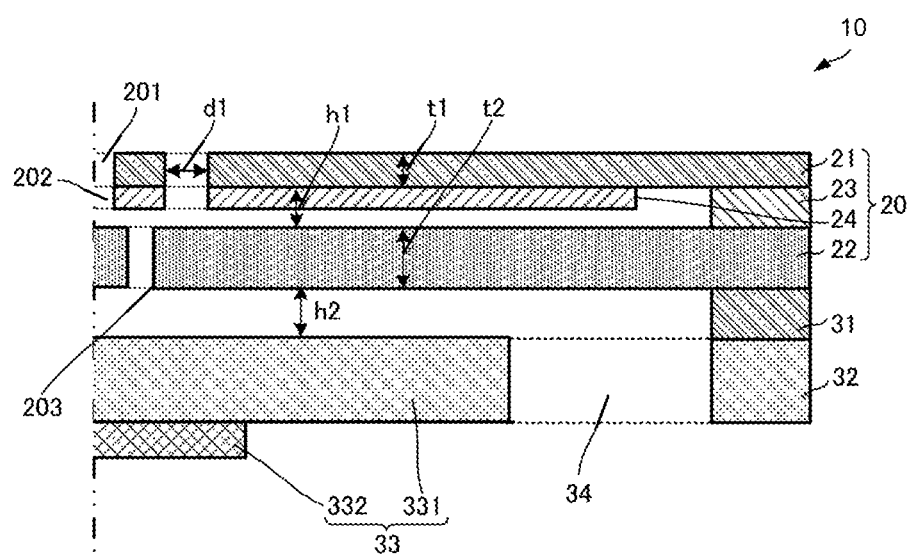
FIG. 4 is an enlarged cross-sectional side view illustrating the fluid control apparatus 10 according to the first embodiment of the present disclosure.
Figure 5A:
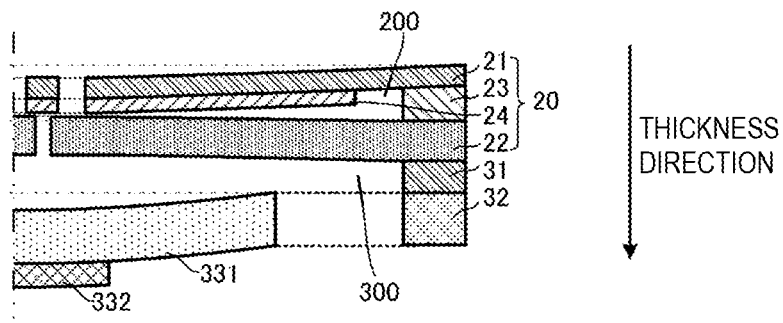
FIG. 5A and FIG. 5B are cross-sectional side views illustrating the fluid control apparatus 10 according to the first embodiment of the present disclosure when the fluid control apparatus 10 deforms.
Figure 5B:
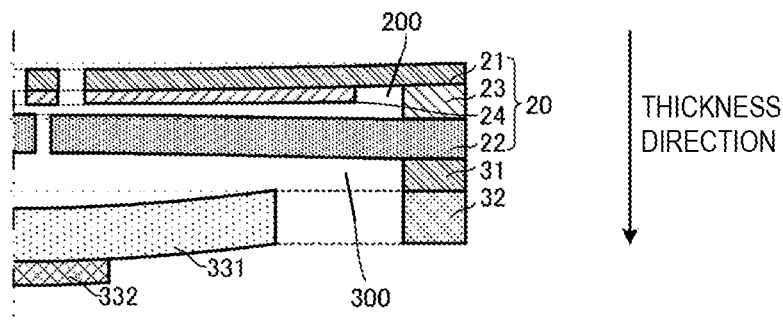
Figure 5C:
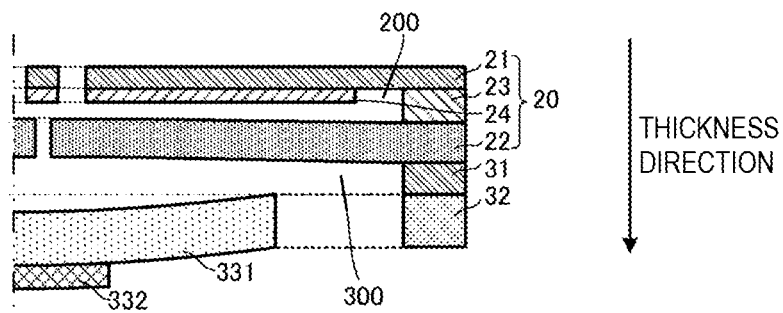
FIG. 5C is a cross-sectional side view illustrating a known fluid control apparatus when the known fluid control apparatus deforms.
Figure 6:
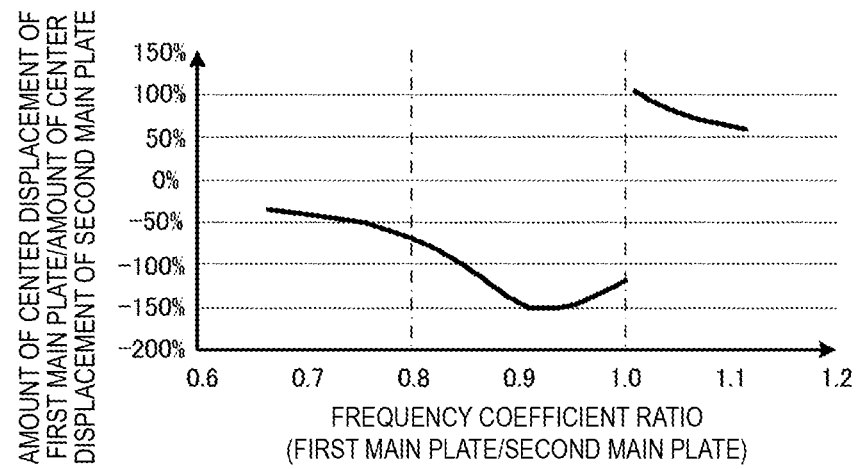
FIG. 6 is a graph depicting displacement percentage with respect to frequency coefficient ratio of the fluid control apparatus 10 according to the first embodiment of the present disclosure.

A fluid control apparatus according to a first embodiment of the present disclosure will be described with reference to the drawings. FIG. 1A is a perspective view illustrating the exterior of a fluid control apparatus 10 according to the first embodiment of the present disclosure when the fluid control apparatus 10 is viewed from the side of a valve 20. FIG. 1B is a perspective view illustrating the exterior of the fluid control apparatus 10 according to the first embodiment of the present disclosure when the fluid control apparatus 10 is viewed from the side of a pump 30. FIG. 2 is an exploded perspective view illustrating the fluid control apparatus 10 according to the first embodiment of the present disclosure. FIG. 3 is a cross-sectional side view of the fluid control apparatus 10, which is taken along line S-S of FIG. 1A and of FIG. 1B. FIG. 4 is an enlarged cross-sectional side view illustrating the fluid control apparatus 10 according to the first embodiment of the present disclosure. FIG. 5A and FIG. 5B are cross-sectional side views illustrating the fluid control apparatus 10 according to the first embodiment of the present disclosure when the fluid control apparatus 10 deforms. FIG. 5C is a cross-sectional side view illustrating a known fluid control apparatus when the known fluid control apparatus deforms. FIG. 6 is a graph depicting displacement percentage with respect to frequency coefficient ratio of the fluid control apparatus 10 according to the first embodiment of the present disclosure. Note that some reference signs are omitted, and a part of the structure is exaggerated for the purpose of easy recognition.

As illustrated in FIGS. 1A and 1B, the fluid control apparatus 10 includes a valve 20 and a pump 30. The valve 20 has multiple first apertures 201 that are opened at a top surface of the valve 20. The first apertures 201 are ventholes.

A structure of the valve 20 will be described first. The valve 20 includes a first main plate 21, a second main plate 22, a side plate 23, and a valve diaphragm 24.

As illustrated in FIGS. 1A, 2, and 3, the first main plate 21 and the second main plate 22 are shaped like discs. The side plate 23 is shaped like a cylinder.

The side plate 23 is disposed between the first main plate 21 and the second main plate 22 and connects these plates to each other so as to enable the first main plate 21 and the second main plate 22 to be opposite to each other. More specifically, the center of the first main plate 21 and the center of the second main plate 22 coincide with each other as viewed in plan. The side plate 23 connects outer peripheral regions of the first main plate 21 and the second main plate 22, which are disposed as described above, along the entire circumferences. Note that the side plate 23 may be integrally formed with the first main plate 21 or with the second main plate 22. In this case, the first main plate 21 or the second main plate 22 may be shaped like a recess.

According to this configuration, the valve 20 has a valve chamber 200 that is a columnar space surrounded by the first main plate 21, the second main plate 22, and the side plate 23.

The valve diaphragm 24 is disposed inside the valve chamber 200.

As described, the first main plate 21 has the first apertures 201 that are formed so as to penetrate the first main plate 21. The valve diaphragm 24 also has multiple second apertures 202 that are formed so as to penetrate the valve diaphragm 24 at the same positions as the first apertures 201 as viewed in plan.

Moreover, the second main plate 22 has multiple third apertures 203 that are formed so as to penetrate the second main plate 22. The third apertures 203, however, are formed so as not to overlap the first apertures 201 nor the second apertures 202 as viewed in plan. The valve chamber 200 of the valve 20 communicates with a pump chamber 300 of the pump 30 through the third apertures 203.

Next, a structure of the pump 30 will be described. As illustrated in FIGS. 1B, 2, and 3, the second main plate 22 also serves as a component of the pump 30. The pump 30 is formed of the second main plate 22, a pump side plate 31, a pump bottom plate 32, and a vibration unit 33. The vibration unit 33 is formed of a vibrating plate 331 and a piezoelectric device 332.

In addition, the pump bottom plate 32 is formed integrally with the vibrating plate 331. More specifically, when the pump 30 is viewed from the second main plate 22, the pump bottom plate 32 and the vibrating plate 331 are connected by connection portions 35 so as to be flush with each other. In other words, the pump bottom plate 32 has multiple pump bottom apertures 34 with a predetermined opening width at positions arranged along the outer periphery of the pump bottom plate 32, and the pump bottom apertures 34 separates the vibrating plate 331 from the pump bottom plate 32. With this configuration, the pump bottom plate 32 holds the vibrating plate 331 in such a manner that the piezoelectric device 332 can vibrate the vibrating plate 331.

The pump side plate 31 is shaped like a ring as viewed from the first main plate 21. The pump side plate 31 is disposed between the second main plate 22 and the pump bottom plate 32 and connects these plates to each other. More specifically, the center of the second main plate 22 and the center of the pump bottom plate 32 coincide with each other. The pump side plate 31 connects outer peripheral regions of the second main plate 22 and the pump bottom plate 32, which are disposed as described above, along the entire circumferences.

According to this configuration, the pump 30 has a pump chamber 300 that is a columnar space surrounded by the second main plate 22, the pump bottom plate 32, and the pump side plate 31.

The piezoelectric device 332 is constituted by a disc-like piezoelectric member and electrodes for driving the piezoelectric member. The electrodes are formed on respective principal surfaces of the disk-like piezoelectric member.

The piezoelectric device 332 is disposed on a surface of the vibrating plate 331 that is opposite to the surface facing the pump chamber 300, in other words, disposed on the outside surface of the pump 30. The center of the piezoelectric device 332 and the center of the vibrating plate 331 substantially coincide with each other as viewed in plan.

The piezoelectric device 332 is coupled to a control unit (not illustrated). The control unit generates drive signals and applies them to the piezoelectric device 332. The drive signals displaces the piezoelectric device 332, and the displacement generates stresses in the vibrating plate 331, which causes the vibrating plate 331 to vibrate flexurally. For example, the vibration of the vibrating plate 331 produces a wave form of Bessel function of the first kind.

Consequently, the flexural vibration of the vibrating plate 331 (i.e., vibration unit 33) changes the volume and the pressure of the pump chamber 300. Accordingly, a fluid drawn in through the pump bottom apertures 34 is discharged through the third apertures 203.

With the above configuration of the valve 20, the fluid flowing in through the third apertures 203 moves the valve diaphragm 24 toward the first main plate 21. As a result, the fluid is discharged out through the second apertures 202 and the first apertures 201. On the other hand, if the fluid tries to flow from the third apertures 203 to the pump bottom apertures 34, the fluid moves the valve diaphragm 24 toward the second main plate 22, and the valve diaphragm 24 thereby plugs the third apertures 203. Accordingly, the fluid control apparatus 10 serves to rectify fluid flow.

The structure of the fluid control apparatus 10 will be described more specifically with reference to FIG. 4. FIG. 4 is an enlarged cross-sectional side view illustrating part of the fluid control apparatus 10 of FIG. 3.

The first main plate 21 and the second main plate 22 are made of such a material and a thicknesses that enable the first main plate 21 and the second main plate 22 to vibrate in a direction normal to the principal surfaces. For example, the material of the first main plate 21 and the second main plate 22 is a stainless steel.

A first main plate thickness t1 of the first main plate 21 is smaller than a second main plate thickness t2 of the second main plate 22.

The first main plate 21 and the second main plate 22 will be compared below by using frequency coefficients obtained from a specific formula in a condition where the first main plate thickness t1<the second main plate thickness t2. The frequency coefficient is a coefficient related to flexibility of the first main plate 21 and the second main plate 22 that vibrate. More specifically, the frequency coefficient is expressed in the following formula, where in a vibrating plate, t is the thickness of the plate, E is the modulus of longitudinal elasticity (i.e., Young's modulus) of the plate, and p is the material density of the plate.

$$\text{frequency coefficient} = t \times \sqrt{\frac{E}{\rho}} \qquad [\text{Math. 1}]$$

In the present embodiment, the first main plate 21 and the second main plate 22 are made of the same material. In this case, the frequency coefficient of the first main plate 21 becomes smaller than the frequency coefficient of the second main plate 22. In other words, the first main plate 21 is more flexible than the second main plate 22.

Accordingly, a phase difference of 90°<θ<270° is produced between the vibration of the first main plate 21 and the vibration of the second main plate 22. In other words, the first main plate 21 and the second main plate 22 vibrate in the opposite phase. In this case, it is preferable that the phase difference be 180° in a vacuum. Note that the phase difference may be 135°<θ<225°. If it is closer to 180°, it is more desirable.

As a result, the displacement of the first main plate 21 becomes large. Accordingly, the change in the gap of the valve chamber 200 becomes large. In other words, opening and closing of the valve are facilitated and the efficiency of the fluid control apparatus 10 is improved.

A gap h1 between the first main plate 21 and the second main plate 22 is set to be smaller than a gap h2 between the second main plate 22 and the vibration unit 33. For example, the gap h1 is in a range from 5 to 100 μm, whereas the gap h2 is in a range from 100 to 500 μm. More desirably, the gap h1 is in a range from 10 to 40 μm, whereas the gap h2 is in a range from 150 to 250 μm.

The pressure in the valve chamber 200 thereby becomes greater than the pressure in the pump chamber 300, which suppresses backflow. In other words, this improves the flow-rectifying effect of the fluid control apparatus 10.

In addition, an opening width d1 of each first aperture 201 is set to be larger than the gap h1 between the first main plate 21 and the second main plate 22. For example, the opening width dl is 0.6 mm in diameter, which is ten or more times greater than the gap h1. Note that the opening width dl is defined as the length of the longest straight line that can be drawn inside the opening of the first aperture 201.

As a result, the flow path resistance when the valve is open is reduced. In other words, this further increases the flow rate in the fluid control apparatus 10.

Referring to FIG. 4 and FIGS. 5A to 5C, deformation of the fluid control apparatus 10 will be described specifically based on results of FEM analyses using an axisymmetric model. Here, the thickness of the vibrating plate 331 is set to be 0.4 mm. Note that the thickness direction refers to a direction in which the first main plate 21, the side plate 23, and the second main plate are stacked in this order. Also, note that in FIGS. 5A to 5C, the deformation of the first main plate 21 and the second main plate 22 are exaggerated.

In FIG. 5A, the first main plate thickness t1 is 0.4 mm, and the second main plate thickness t2 is 0.45 mm. In this case, the first main plate 21 and the second main plate 22 vibrate in the opposite phase, and the first main plate 21 and the second main plate 22 are displaced in opposite directions. The displacement of the first main plate 21 and the displacement of the second main plate 22 in the thickness direction are largest. Consequently, the gap of the valve chamber 200 changes most greatly.

Next, as in the FIG. 5B, the first main plate thickness t1 is set to be 0.3 mm, and the second main plate thickness t2 is set to be 0.45 mm. In this case, the first main plate 21 and the second main plate 22 also vibrate in the opposite phase although it is less efficient compared with the configuration of FIG. 5A. The displacement of the first main plate 21 and the displacement of the second main plate 22 in the thickness direction are still large and are in opposite directions. Accordingly, the gap of the valve chamber 200 changes greatly.

The configuration in FIG. 5C is based on a known fluid control apparatus, in which the first main plate thickness t1 is set to be 0.5 mm, and the second main plate thickness t2 is set to be 0.45 mm. Due to the first main plate thickness t1 being greater than the second main plate thickness t2, the displacement of the first main plate 21 and the displacement of the second main plate 22 become smaller. Accordingly, the change in the gap of the valve chamber 200 is small.

In summary, the largest displacement of the first main plate 21 and the second main plate 22 can be obtained by setting the first main plate thickness t1 to be 0.4 mm and the second main plate thickness t2 to be 0.45 mm in accordance with the configuration in FIG. 5A. In this case, the phase difference between the first main plate 21 and the second main plate 22 comes closer to 180°. In other words, opening and closing of the valve are facilitated and the efficiency of the fluid control apparatus 10 is improved.

FIG. 6 is a graph depicting simulation results of displacement percentage with respect to frequency coefficient ratio in the fluid control apparatus 10.

In the case illustrated in FIG. 6, the second main plate thickness t2 is set to be 0.45 mm, and the thickness of the vibrating plate 331 is set to be 0.4 mm. The first main plate thickness t1 is varied in a range between 0.3 mm and 0.5 mm.

The transverse axis represents frequency coefficient ratio. The frequency coefficient ratio is obtained from the following formula: frequency coefficient of first main plate 21/frequency coefficient of second main plate 22. The vertical axis represents displacement ratio. The displacement ratio is obtained from the following formula: amount of center displacement of first main plate 21/amount of center displacement of second main plate 22.

As illustrated in FIG. 6, in the case of the frequency coefficient ratio being less than one, the displacement of the first main plate 21 becomes larger than the displacement of the second main plate 22, and the first main plate 21 and the second main plate 22 are displaced in the opposite phase, which causes the gap in the valve chamber 200 to become larger. Especially when the frequency coefficient ratio of the first main plate 21 to the second main plate 22 is greater than 0.85 and smaller than 1, the first main plate 21 and the second main plate 22 are displaced in the opposite phase, and an absolute amount of displacement of the valve chamber 200 (i.e., amount of change in the gap) becomes greatest. Accordingly, performance of the fluid control apparatus 10 is improved. On the other hand, in the case of the frequency coefficient ratio being greater than one, the first main plate 21 and the second main plate 22 are displaced in phase, which causes the change in the gap of the valve chamber 200 to become small.

The shape of the fluid control apparatus 10 has been described as the substantially disc-like shape. However, the shape of the fluid control apparatus 10 is not limited to the disc-like shape but may be a shape close to a polygon.

In addition, the first main plate 21 and the second main plate 22 have been described as being made of the same material, for example, a stainless steel. However, the material of the first main plate 21 and the material of the second main plate 22 need not be the same. A different material may be used insofar as the material provides the first main plate 21 with flexibility and with the frequency coefficient smaller than that of the second main plate 22. The same advantageous effects can be thereby obtained.

The above-described fluid control apparatus is applied, for example, to a medical apparatus, such as a sphygmomanometer, a massage machine, an aspirator, a nebulizer, or a device for negative pressure wound therapy. The fluid control apparatus can improve operation efficiency of such a medical apparatus.

Note that in the present disclosure, the first main plate and the second main plate have been described as flat plates having uniform thicknesses. However, in the case of the first main plate and the second main plate each having uneven thickness, the average thickness of the first main plate and the average thickness of the second main plate can be compared and be set so as to satisfy the following inequality: average thickness t1a of first main plate 21<average thickness t2a of second main plate 22.

d1 opening width
h1, h2 gap
t1 first main plate thickness
t2 second main plate thickness
fluid control apparatus
20 valve
21 first main plate
22 second main plate
23 side plate
24 valve diaphragm
30 pump
31 pump side plate
32 pump bottom plate
33 vibration unit
34 pump bottom aperture
35 connection portion
200 valve chamber
201 first aperture
202 second aperture
203 third aperture
300 pump chamber
331 vibrating plate
332 piezoelectric device

The invention claimed is:
1. A fluid control apparatus, comprising:
a valve including
a first main plate,
a second main plate having one principal surface opposite to one principal surface of the first main plate, and
a side plate connecting the first main plate and the second main plate to each other,
the valve having a valve chamber surrounded by the first main plate, the second main plate, and the side plate,
the first main plate having one or more first apertures through which the valve chamber communicates with outside of the valve chamber, the second main plate having a second aperture through which the valve chamber communicates with outside of the valve chamber, the valve further including
a valve diaphragm disposed inside the valve chamber, the valve diaphragm being configured to switch between a state in which the first aperture and the second aperture communicate with each other and a state in which the first aperture and the second aperture do not communicate with each other; and a pump including
a vibration unit having a piezoelectric device and a vibrating plate and disposed so as to be opposite to another principal surface of the second main plate,
the pump having a pump chamber defined by the vibration unit and the second main plate,
the pump chamber communicating with the valve chamber through the second aperture, wherein
in flexural vibration of the vibration unit, a frequency coefficient of the first main plate is smaller than a frequency coefficient of the second main plate,
the first main plate has a plurality of the first apertures, and
a gap between the first main plate and the second main plate is smaller than a minimum opening width of each of the first apertures.

2. The fluid control apparatus according to claim 1, wherein
the gap between the first main plate and the second main plate is smaller than a gap between the vibration unit and the second main plate.

3. A medical apparatus, comprising:
the fluid control apparatus according to claim 2.

4. A medical apparatus, comprising:
the fluid control apparatus according to claim 1.

5. A fluid control apparatus, comprising:
a valve including
a first main plate,
a second main plate having one principal surface opposite to one principal surface of the first main plate, and
a side plate connecting the first main plate and the second main plate to each other,
the valve having a valve chamber surrounded by the first main plate, the second main plate, and the side plate,
the first main plate having one or more first apertures through which the valve chamber communicates with outside of the valve chamber,
the second main plate having a second aperture through which the valve chamber communicates with outside of the valve chamber,
the valve further including
a valve diaphragm disposed inside the valve chamber, the valve diaphragm being configured to switch between a state in which the first aperture and the second aperture communicate with each other and a state in which the first aperture and the second aperture do not communicate with each other; and
a pump including
a vibration unit having a piezoelectric device and a vibrating plate and disposed so as to be opposite to another principal surface of the second main plate,
the pump having a pump chamber defined by the vibration unit and the second main plate,
the pump chamber communicating with the valve chamber through the second aperture, wherein in flexural vibration of the vibration unit, a frequency coefficient of the first main plate is smaller than a frequency coefficient of the second main plate, and
a frequency coefficient ratio of the first main plate to the second main plate is greater than 0.85 and smaller than 1.

6. A medical apparatus, comprising:
the fluid control apparatus according to claim 5.

7. The fluid control apparatus according to claim 5, wherein
the first main plate has a plurality of the first apertures, and
a gap between the first main plate and the second main plate is smaller than a minimum opening width of each of the first apertures.

8. A fluid control apparatus, comprising:
a valve including
a first main plate,
a second main plate having one principal surface opposite to one principal surface of the first main plate, and
a side plate connecting the first main plate and the second main plate to each other,
the valve having a valve chamber surrounded by the first main plate, the second main plate, and the side plate,
the first main plate having one or more first apertures through which the valve chamber communicates with outside of the valve chamber,
the second main plate having a second aperture through which the valve chamber communicates with outside of the valve chamber,
the valve further including
a valve diaphragm disposed inside the valve chamber, the valve diaphragm being configured to switch between a state in which the first aperture and the second aperture communicate with each other and a state in which the first aperture and the second aperture do not communicate with each other; and
a pump including
a vibration unit having a piezoelectric device and a vibrating plate and disposed so as to be opposite to another principal surface of the second main plate,
the pump having a pump chamber defined by the vibration unit and the second main plate,
the pump chamber communicating with the valve chamber through the second aperture, wherein
the first main plate and the second main plate are comprised of the same material,
a thickness of the first main plate is smaller than a thickness of the second main plate in a direction normal to respective principal surfaces,
the first main plate has a plurality of the first apertures, and
a gap between the first main plate and the second main plate is smaller than a minimum opening width of each of the first apertures.

9. A medical apparatus, comprising:
the fluid control apparatus according to claim 8.

10. A fluid control apparatus, comprising:
a valve including
a first main plate,
a second main plate having one principal surface opposite to one principal surface of the first main plate, and a side plate connecting the first main plate and the second main plate to each other, the valve having a valve chamber surrounded by the first main plate, the second main plate, and the side plate, the first main plate having one or more first apertures through which the valve chamber communicates with outside of the valve chamber, the second main plate having a second aperture through which the valve chamber communicates with outside of the valve chamber, the valve further including a valve diaphragm disposed inside the valve chamber, the valve diaphragm being configured to switch between a state in which the first aperture and the second aperture communicate with each other and a state in which the first aperture and the second aperture do not communicate with each other; and a pump including a vibration unit having a piezoelectric device and a vibrating plate and disposed so as to be opposite to another principal surface of the second main plate, the pump having a pump chamber defined by the vibration unit and the second main plate, the pump chamber communicating with the valve chamber through the second aperture, wherein the first main plate and the second main plate are comprised of the same material, a thickness of the first main plate is smaller than a thickness of the second main plate in a direction normal to respective principal surfaces, and a frequency coefficient ratio of the first main plate to the second main plate is greater than 0.85 and smaller than 1.

11. A medical apparatus, comprising:
the fluid control apparatus according to claim 10.

* * * * *